United States Patent [19]

Spencer

[11] 4,432,989
[45] Feb. 21, 1984

[54] α-ARYL-1H-IMIDAZOLE-1-ETHANOLS
[75] Inventor: Homer K. Spencer, Randolph, N.J.
[73] Assignee: Sandoz, Inc., E. Hanover, N.J.
[21] Appl. No.: 372,296
[22] Filed: Apr. 27, 1982

Related U.S. Application Data

[63] Continuation of Ser. No. 170,982, Jul. 18, 1980, abandoned, which is a continuation-in-part of Ser. No. 93,800, Nov. 13, 1979, abandoned.

[51] Int. Cl.$^3$ .................. C07D 233/64; A61K 31/415
[52] U.S. Cl. ............................... 424/273 R; 548/341; 548/336
[58] Field of Search .................... 424/273 R; 548/341, 548/336

[56] References Cited

U.S. PATENT DOCUMENTS 3,839,574 10/1974 Godefroi et al. ................... 548/341

FOREIGN PATENT DOCUMENTS 54-27563  3/1979  Japan ................................. 548/341

OTHER PUBLICATIONS

Godefroi et al., (II) Chem. Abs., vol. 72, 1970, 90466V.
Timmler et al., Chem. Abst., 88:152617m.

*Primary Examiner*—Jane T. Fan
*Attorney, Agent, or Firm*—Gerald D. Sharkin; Richard E. Vila

[57] ABSTRACT

Fungicides of the formula:

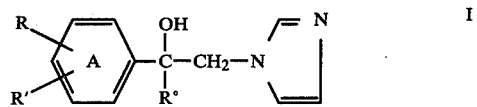

wherein
R° is alkyl of 2 to 6 carbon atoms, cycloalkyl of 3 to 6 carbon atoms, cycloalkylalkyl in which the cycloalkyl is of 3 to 6 carbon atoms and the alkyl portion of 1 to 3 carbon atoms, said cycloalkyl and cycloalkylalkyl being optionally ring substituted by one or two alkyl groups of 1 to 3 carbon atoms, and R is hydrogen, fluoro, chloro, bromo, alkyl of 1 to 4 carbon atoms, alkoxy of 1 to 4 carbon atoms, alkylthio of 1 to 4 carbon atoms or nitro, and R' is hydrogen, fluoro, chloro, bromo, alkyl of 1 to 4 carbon atoms, alkoxy of 1 to 4 carbon atoms, alkylthio of 1 to 4 carbon atoms, —CF$_3$ in the 3-position of Ring A, nitro, —CN, —COOR", an optionally substituted phenyl group of the formula:

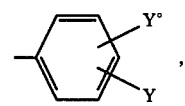

or an optionally substituted phenoxy group in the 4-position of Ring A and having the formula:

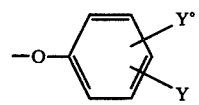

R" is hydrogen, alkyl of 1 to 4 carbon atoms or cation, or

R and R' together represent alkylenedioxy of 1 or 2 carbon atoms substituted onto adjacent carbon atoms of the phenyl Ring A, and Y° and Y are independently hydrogen, fluoro, chloro, bromo, alkyl of 1 to 4 carbon atoms or alkoxy of 1 to 4 carbon atoms, with the proviso that when R° is n-butyl: (a) at least one of R and R' is other than hydrogen and (b) R and R' are not both halo.

13 Claims, No Drawings

αARYL-1H-IMIDAZOLE-1-ETHANOLS

This is a continuation of application Ser. No. 170,982 filed July 18, 1980, which in turn is a continuation-in-part of Ser. No. 93,800, filed Nov. 13, 1979 now both abandoned.

The present invention relates to α-aryl-1H-imidazole-1-ethanols, more particularly α-alkyl or cycloalkyl-α-phenyl-1H-imidazole-1-ethanols, their use as fungicides and agricultural compositions for facilitating such use.

The compounds of the present invention may be represented structurally by the following formula I:

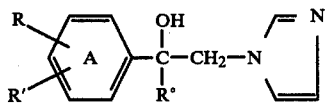

wherein
R° is alkyl of 2 to 6 carbon atoms, cycloalkyl of 3 to 6 carbon atoms, cycloalkylalkyl in which the cycloalkyl is of 3 to 6 carbon atoms and the alkyl portion of 1 to 3 carbon atoms, said cycloalkyl and cycloalkylalkyl being optionally ring substituted by one or two alkyl groups of 1 to 3 carbon atoms, and R is hydrogen, fluoro, chloro, bromo, alkyl of 1 to 4 carbon atoms, alkoxy of 1 to 4 carbon atoms, alkylthio of 1 to 4 carbon atoms or nitro, and R' is hydrogen, fluoro, chloro, bromo, alkyl of 1 to 4 carbon atoms, alkoxy of 1 to 4 carbon atoms, alkylthio of 1 to 4 carbon atoms, —CF$_3$ in the 3-position of Ring A, nitro, —CN, —COOR", an optionally substituted phenyl group of the formula:

or an optionally substituted phenoxy group in the 4-position of Ring A and having the formula:

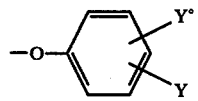

R" is hydrogen, alkyl of 1 to 4 carbon atoms or a cation, preferably an agriculturally acceptable cation, or R and R' together represent alkylenedioxy of 1 or 2 carbon atoms substituted onto adjacent carbon atoms of the phenyl Ring A, and Y° and Y are independently hydrogen, fluoro, chloro, bromo, alkyl of 1 to 4 carbon atoms or alkoxy of 1 to 4 carbon atoms, with the proviso that when R° is n-butyl: (a) at least one of R and R' is other than hydrogen and (b) R and R' are not both halo.

The compounds of the formula I may be prepared in a process (a) by reacting a compound of the formula II:

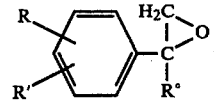

wherein R°, R and R' are as above defined, with a compound of the formula III

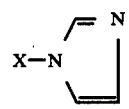

wherein X is an alkali metal, eg. sodium, in an inert organic solvent.

The process (a) may be carried out at temperatures typically from 0° C. to 160° C., preferably 40° C. to 100° C., in an inert organic solvent of conventional type, such as dimethylformamide. As is conventional, the compound of the formula III is preferably provided by reacting imidazole with a strong base such as an alkali metal hydride in an inert organic solvent which is conveniently the same solvent which is to be used in process (a). The reaction product of the formula I may be recovered from the reaction mixture in which it is formed by working up by established procedures.

The compounds of the formula I in which R" is a cation may be prepared by conventional procedures from the compounds in which R" is hydrogen or alkyl, such as by routine neutralization of the compounds in which R" is hydrogen with a base having the cation desired to be introduced as the R" significance. The compounds I where R" is a cation may be employed to produce an analogous compound I in which R" is a different cation by employing conventional procedures including ion exchange techniques, whereby, for example, a non-agriculturally acceptable cation may be exchanged to provide an agriculturally acceptable cation. It is generally preferred to prepare the compounds I in which R" is a cation by employing reagents directly resulting in a compound in which R" is an agricultural cation and hence suitable for fungicidal use in accordance with the invention. Representative agriculturally acceptable cations include by way of illustration only the sodium, potassium and ammonium cations.

The compounds of the formula II may be prepared in a process (b) by reacting a compound of the formula IV:

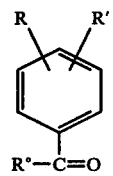

wherein R°, R and R' are as above defined, with the reaction product of a strong base and trimethylsulfonium iodide which provides a reagent which may be represented by the formula V:

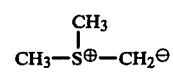

which process (b) is carried out in an inert organic solvent.

Process (b) is a known type reaction for preparation of epoxy derivatives from ketones. The process may be suitably carried out at temperatures of from minus 40° C. to plus 70° C., preferably from about minus 10° C. to plus 30° C., and in an inert solvent of conventional type, eg. dimethylsulfoxide, tetrahydrofuran and the like. The compound of the formula V is preferably provided in a conventional manner by reacting trimethylsulfonium iodide with a strong base, eg. an alkali metal hydride such as sodium hydride, or the reaction product of sodium hydride and dimethylsulfoxide (a so-called "Dimsyl anion"), at temperatures typically of the order of minus 20° C. to plus 20° C. and in an inert organic solvent which is preferably a solvent similar to or otherwise useful as the solvent for process (b). The reaction product of the formula II may be recovered from the reaction mixture of process (b) by working up by established procedures.

Many of the compounds of the formula IV are known and those which are not known per se may be prepared from known materials by procedures analogous to those known for preparation of the known compounds. Many of the compounds II are also known. Other synthetic procedures for compounds I may also be found in the literature.

The compounds of the formula I are useful as fungicides in combatting phytopathogenic fungus, including particularly powdery mildew and rust fungi, as indicated by standard in vivo and in vitro tests of the type hereinafter illustrated. For such use the compounds of the formula I may be applied to plants, seed or soil in a manner conventional in the use of fungicidal agents. As will be appreciated, the amount of the compound of the formula I to be applied will vary depending upon known factors such as the particular compound employed, whether the treatment is prophylactic or therapeutic, whether the compound is applied as a foliar spray, a soil treatment or a seed dressing, the species of fungus under treatment and the time of application. However, in general, satisfactory results are obtained when the compound is applied to a crop locus, either on crops or to soil, at a rate of from about 0.01 to 5, preferably about 0.1 to 2 kg (active ingredient)/hectare. The treatment may be repeated as required, e.g. at 8 to 30 day intervals. When employed as a seed dressing, satisfactory results are obtained when the compound is employed at a rate of from about 0.05 to 0.5, preferably about 0.1 to 0.3 g/kg seed.

The term "soil" as used herein is intended to embrace any conventional growing medium whether natural or artificial.

The invention also provides, as an additional feature, fungicidal compositions, comprising, as fungicide, a compound of formula I and an inert fungicide carrier. In general, such compositions contain from about 0.01 to 90, preferably from about 0.1 to 60% by weight of active agent. They may be in concentrate form, for dilution down prior to application, or in dilute, ready to apply, form. As examples of particular forms may be given wettable powder, emulsion concentrate, dusting, spraying, granulate and delayed release forms, incorporating conventional carriers and such other diluents and/or adjuvants acceptable in the agricultural art. Application forms of those compositions generally contain between about 0.01 and 10% by weight of a compound of formula I as active agent. Concentrate forms of compositions for fungicide use generally contain between about 2 and 80%, preferably between about 5 and 70%, by weight of a compound of formula I as active agent. Emulsion concentrate forms generally contain from about 10 to 70%, preferably about 20 to 60% by weight of active ingredient. Solid, particulate compositions are preferred.

The compositions particularly adapted for spraying preferably include a surfactant such as a liquid polyglycol ether, a fatty alkyl sulphate or a lignin sulphonate.

In addition to conventional carrier and surface-active materials, formulations of the compound I of the invention may also contain further additives with special purposes e.g. stabilizers, deactivators (for solid formulations on carriers with an active surface), agents for improving the adhesion to plants, corrosion inhibitors, anti-foaming agents and colorants.

Moreover, further fungicides, bactericides or other beneficially-acting materials, such as insecticides, may be present in the formulations and are contemplated as further embodiments of this invention.

Examples of the production of fungicide formulations are as follows:

(a) Wettable powder formulation 50 parts of α-t-butyl-α-(p-methylphenyl)-1H-imidazole-1-ethanol are ground with 2 parts of lauryl sulphate, 3 parts sodium lignin sulphonate and 45 parts of finely divided kaolinite until the mean particle size is below 5 microns. The resulting wettable powder so obtained is diluted with water before use to a concentration of between 0.01% to 5% active agent. The resulting spray liquor may be applied by foliar spray as well as by root drench application.

(b) Granulate formulation

Onto 94.5 parts by weight of quartz sand in a tumbler mixer is sprayed 0.5 parts by weight of a binder (non-ionic tenside) and the whole thoroughly mixed. 5 parts by weight of powdered α-t-butyl-α-(p-methylphenyl)-1H-imidazole-1-ethanol are then added and thorough mixing continued to obtain a granulate formulation with a particle size in the range of from 0.3 to 0.7 mm. The granulate may be applied by incorporation into the soil adjacent the plants to be treated.

(c) Emulsion Concentrate 25 parts by weight of α-t-butyl-α-(p-methylphenyl)-1H-imidazole-1-ethanol are mixed with 30 parts by weight of iso-octyl phenyl octaglycol ether and 45 parts by weight of a petroleum fraction with a boiling range of 210°–280° C. ($D_{20}$:0.92). The concentrate is diluted with water to the desired concentration.

(d) Seed dressing 45 parts of a compound of α-t-butyl-α-(p-methylphenyl)-1H-imidazole-1-ethanol are mixed with 1.5 parts of diamylphenoldecaglycolether ethylene oxide adduct, 2 parts of spindle oil, 51 parts of fine talcum and 0.5 parts of colorant rhodamin B. The mixture is ground in a contraplex mill at 10,000 rpm until an average particle size of less than 20 microns is obtained. The resulting dry seed dressing powder has good adherance and may be applied to seeds, e.g. by mixing for 2 to 5 minutes in a slowly turning vessel.

Fungi against which the compounds of the formula I are indicated to be particularly of interest include by way of illustration the following:

(A) those of the Order Uredinales such as those of the genus Uromyces in plants such as beans, e.g. *Uromyces appendiculatus,* and ornamentals, e.g. *Uromyces dianthi,* those of the genus Hemileia in plants such as coffee, e.g.

*Hemileia vastatrix*, those of the genus Puccinia in plants such as cereals (e.g. wheat, oats, barley) e.g. *Puccinia graminis, Puccinia recondita* and *Puccinia striiformis*, or ornamentals, e.g. *Puccinia pelargoniizonalis*, those of the genus Phakopsora in plants such as soya, e.g. *Phakopsora pachyrhizi*, those of the genus Melampsora in plants such as flax, e.g. *Melampsora lini*, and those of the genus Tranzschelia, e.g. *Tranzschelia pruni* in plums;

(B) those of the Order Erysiphales such as those of the genus Erysiphe in plants such as cucumber, barley, wheat and sugarbeet, eg. *Erysiphe graminis f.sp. tritici* on wheat and *Erysiphe cichoraceareum on cucumbers;* those of the genus Sphaerotheca on cucumbers and roses, eg. *Spkhaerotheca pannosa* on roses; those of the genus Podosphera in apples, pears and prunes, eg. *Podosphaera leucotricha* on apples; those of the genus Uncinula on plants such as grapes, eg. *Uncinula necator* on grapevine; those of the genus Oidium on a wide variety of plants; and those of the genus Leveillula in plants such as cotton and other nalvaceae, eg. *Leveillula taurica* on cotton.

(C) those belonging to the heterogenous group of the Deuteromycetes such as those of the genus Helminthosporium in plants such as barley and corn, eg. Helm. Sativum; those of the genus Septoria in plants such wheat, tomato and celery, eg. *Sept. tritici* in wheat; and those of the genus Rhizoctonia in plants such as cotton and potato, eg. Rhiz. Solani in cotton;

(D) those of the order Ustilagenales such as those of the genus Ustilago in plants such as barley, wheat, corn and sugarcane, eg. *U. maydis* on corn and *U. nuda*, and (E) those of the genus Fusarium spp, eg. *F. oxysporum* f. sp. *lycopersici* in tomato, *F. oxysporum* f. sp. *vasinfectum* in cotton, *F. oxysporum* f. sp. *cubense* in banana, *F. solani* in vegetables, *F. culmorum* in cereals and *F. graminearum* in cereals.

(F) those of the genus Phoma spp., eg. Ph. *betae* on sugar beet;

(G) those of the genus Stereum spp., eg. stereum purpurem in pip and stone fruit trees;

(H) those of the genus Phytophthora spp., eg. Ph. *cactorum*, Ph. *parasitica* and Ph. *cinamomi* on susceptible plants;

(I) *Thielaviopsis basicola* which is found on a wide variety of crops; (J) those of the genus Aphancymces spp., eg. *Aphancmyces cuteiches;*

(K) those of the genus Piricularia spp., eg. *P. oryzae* on rice; and (L) those of the genus Colletotrichum spp., eg. *C. lindemuthianum* in beans.

The following conventional tests are illustrative of the manner by which the fungicidal activity of the compounds of the formula I may be indicated.

Test Method A: In vivo employing bean rust (*Uromyces appendiculatus*). *Phaseolus vulgaris* (pole bean plant) is cultivated in a mixture of peat and sand in plastic pots of 6 cm diameter for 9 days. The plants are sprayed with a spray liquor containing 0.0008 to 0.05% (eg. at 0.0008%, 0.003%, 0.012% and 0.05%) active ingredient. Treatment comprises foliar spraying to near run-off or soil drenching (28 ml of spray liquor per pot). After drying, the plants are inoculated with a spore suspension spray (500,000 to 700,000 spores/ml) and incubated for 7 days in an incubation chamber at 100% relative humidity and 21°. The efficacy of the active agent treatment is determined by comparing the number of pustules/leaf with that on untreated, similarly inoculated check plants. The compound of Example 1, hereinafter, used in the wettable powder formulation given above provides a significant degree of fungicidal activity in the above test, both by contact as well as root-systemic action.

Analogous tests are run on the following crop/fungi with similar results.
Coffee: coffee leaf rust (*Hemileia vastatrix*)
Wheat: black stem rust (*Puccinia graminis*)
Wheat: brown leaf rust (*Puccinia recondita*)
Wheat: yellow or stripe rust (*Puccinia striiformis*)
Flax: flax rust (*Melamspora Lini*)
Pelargonium: Pelargonium rust (*Puccinia pelargoniizonalis*)
Snapdragon: Snapdragon rust (*Puccinia antirrhini*)

Test Method B: In vivo employing cucumber powdery mildew (*Erysiphe cichoracearum*). *Cucumis sativus* (cucumber) is cultivated in a mixture of peat and sand in plastic pots of 6 cm diameter for 7 days. The plants are sprayed with a spray liquor containing 0.0008 to 0.05% (eg. at 0.0008%, 0.003%, 0.012% and 0.05%) active ingredient. Treatment comprises foliar spraying to near run-off or soil drenching (28 ml. of spray liquor per pot). After drying, the plants are inoculated by dusting them with freshly collected conidia and are then incubated for 7 days in an incubation chamber at 60-80% relative humidity and 25°-30° C. The efficacy of the active ingredient is determined by comparing the degree of fungal attack with that on untreated, similarly inoculated check plants. The compound of Example 1, hereinafter, used in the wettable powder formulation given above provides a significant degree of fungicidal activity, both by contact as well as root-systemic action.

Tests analogous to Test Method B are made with similar results on the following crop/fungi:
wheat: wheat powdery mildew (*Erys, gram.* f.sp. *tritici*)
Barley: barley powdery mildew (*Erys, Gram.* f.sp. *hordei*)
Apple: apple powdery mildew (*Podos leucotricha*)
Grape: grapevine powdery mildew (*Uncinula necator*)

Test Method B, above, as regards cucumber powdery mildew and the preferred compound of Example 1, hereinafter is repeated (both foliar spray and soil drench) but at the lower concentrations of 0.0002% and 0.00005% with the result that 100% and 80%, respectively, control of the fungi is still obtained by spray application and 55% and 10%, respectively by soil drenching thereby still further indicating the outstanding potency provided by the invention.

Test method C; In vitro test employing *Ustilago maydis* (corn smut). Different concentrations of the active ingredient are incorporated in malt agar plates to give concentrations of 0.8 to 200 ppm a.i. (eg. at 0.8, 3.2, 12.5, 50 and 200 ppm). The plates are then inoculated by spraying a spore suspension of *U. maydis* onto them or placing an agar plug containing the fungus in the center of the plate. The plates are incubated at room temperature for 2-5 days. The efficacy of the active agent treatment is determined by comparing the growth of the fungus with that in untreated, similarly inoculated plates. The compound of Example 1 hereinafter provides some control in Test Method C at the higher concentration and good control at the lower and higher concentrations in analogous test on *Fusarium oxysporum* f.sp.

Additional tests analogous to Test Method C at 13, 50 and 200 ppm a.i. show except where noted a 100% control with the compound of Example 1 hereinafter at at least one test dosage on the following: *Phytophthora cactorum* (maximum control 85%); *Phytophthora cinamomi* (maximum control 65%); *Aphanomyces euteiches; Stereum purpureum; Thielaviopsis basicola* (maximum control 80%); *Piricularia oryzae* (maximum control 70%); and *Colletotrichum lindemuthianum* (maximum control 65%).

Fungi of the aforementioned genera cause considerable damage in agriculture and are difficult to prevent or control. In addition to combatting such fungi, the compounds of the formula I are indicated to be non-phytotoxic at effective doses in plants subject to such fungi and are further indicated to be of particular interest as also acting to combat fungi by systemic action as determined, for example, in the combatting of *Uromyces appendiculatus* on beans.

Additional tests analogous to Test Methods A and B at doses of 32, 125 and 500 ppm a.i. conducted with the compound of Example 1 hereinafter show by spray application a 60%, 80% and 90% control, respectively of Helminthosporium on barley with no phytotoxity.

Test Method D: In vivo, employing Rhizoctonia Solani. The fungus is cultivated in a sterile mixture of Zonolite and corn meal (10:1 w/w) to which water is added in a ratio of about 1:1 (w/w); cultivation lasts for 14 days at 25° C. The fungus is then mixed into a semi-sterile mixture of peat and sand which then is treated with a suspension containing the formulated active ingredient to give concentration of 10 to 160 ppm (eg. 10, 40 and 160 ppm calculated per volume) substrate. The substrate is transferred to pots of 5 cm diameter which are planted with cotton seedling (cotyledonous stage). The planted pots are incubated at 24° C. and 60–70% relative humidity in an incubation chamber for 14 days, after which disease attack is determined by comparing the fungal attack on roots and hypocotyl with that on untreated, similarly inoculated check plants. The compound of Example 1, hereinafter, used in the wettable powder formulation given above provides 100% disease control with no phytotoxicity at the higher dose, and 70% control at the intermediate dose.

A test analogous to Test Method D is run with *Phoma betae* on sugar beet to give 100% control with 20% phytotoxicity at the lower dose.

From the foregoing it will be evident to those skilled in the art that the compounds of the present invention are also indicated to be of particular interest with regard to the control of important soil- and seed-borne fungi, eg. Helminthosporium, Phoma, Rhizoctonia and Thielaviopsis, in addition to their considerable interest and value in the control of powdery mildews and rusts.

The particular value and advantages of the invention are confirmed and/or further indicated in more detailed evaluations of the preferred compound of Example 1 hereinafter which exhibits the following very desirable properties: (1) a persistency of action that still produces 70% control of uromyces app. on pole beans at spray concentrations of 0.012% on application 8 days before inoculation; (2) a good stability of aqueous spray suspensions as indicated by 100% control of uromyces app. on pole beans on application 3 days after preparation of the suspension (0.012% concentration); (3) rapid and lasting penetration of the active substance into leaves of plants to be protected as indicated by 80% control at the 0.012% concentration after washing the leaves of grapevine for 15 minutes 2 hours after application of the active ingredient followed by infestation with uncinula, (4) a 65% control in simulated rain washing of the leaves of coffee plants at a rain rate of 50 MM/hour first applied two hours after application of the active ingredient for 15 minutes followed by drying and a second application of rain for 15 minutes again, followed by infestation of the coffee plant with *Hemileia vastatrix*, and (5) a 60% control in simulated rain washing of the leaves of pole beans at a rain rate of 50 MM/hour first applied 2 hours after application of the active ingredient for 10 minutes, followed by infestation of the pole bean plants with Uromyces app. In still further evaluation of the preferred compound of Example 1 hereinafter a fungicidal activity of 100% compared with untreated standard is obtained on application of the active ingredient at a concentration of 0.012% 1 day after pole beans are infested with Uromyces, and a 60% control 2 days after infestation.

Other compounds of the formula I as given in Example 2, hereinafter, also show very good to outstanding fungicidal activity in evaluation procedures as above described.

Preferred compounds of the formula I have one or more and preferably all of the following features: (a) R° is branched alkyl of 4 to 6 carbon atoms, cycloalkyl of 3 to 6 carbon atoms or cycloalkylmethyl in which the cycloalkyl portion is of 3 to 6 carbon atoms; (b) R is hydrogen, fluoro, chloro, bromo or $C_1$–$C_4$ alkyl; (c) R' is hydrogen, fluoro, chloro, bromo, $C_1$–$C_4$ alkyl, $C_1$–$C_4$ alkoxy or $C_1$–$C_4$ alkylthio or (d) R' is one of the groups

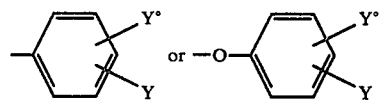

located at the para-position of Ring A, and (c) the compounds of the formula I in free base form. The more preferred among the above-mentioned preferred compounds of the formula I have one or more and preferably all of the following features: (a) R° is branched alkyl of 4 or 5 carbon atoms or cycloalkyl of 3 to 6 carbon atoms; R is hydrogen, fluoro, chloro or $C_1$–$C_2$ alkyl and (c) R' is hydrogen, fluoro, chloro, bromo, $C_1$–$C_2$ alkyl or $C_1$–$C_2$ alkoxy; or (d) R is hydrogen and R' is

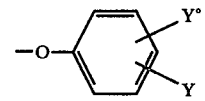

located at the para-position of Ring A, more preferably with Y° and Y being hydrogen.

In general, R° is preferably a branched butyl, ie. sec-butyl, isobutyl or t-butyl, but most preferably R° is t-butyl.

In general, it is preferred that at least one of R and R' be other than hydrogen, particularly alkyl, eg. methyl at the para-position of Ring A, usually with the other being hydrogen.

The compounds of the formula I in which R" is other than a cation may be prepared and used in the form of acid addition salts. Such forms are generally equivalent to the free base forms and accordingly included with the scope of the invention. The acids more typically used in preparing such acid addition salt forms include by way of illustration only hydrochloric, hydrobromic, sulfuric, nitric and oxalic acid. The preferred acid addition salt forms are the agriculturally acceptable salt forms which are useful in the methods and compositions of the invention. The acid addition salt forms can be prepared from the free base forms by conventional procedures. Conversely, the free base forms can be prepared from the acid addition salt forms by conventional procedures. The acid addition salt forms which are not agriculturally acceptable may be used in the preparation of the free base form or agriculturally acceptable form by the conventional procedures.

The following examples further illustrate the present invention.

EXAMPLE 1

α-t-butyl-α-(p-methylphenyl)-1H-imidazole-1-ethanol

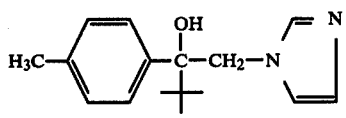

A 0.82 g. portion of 61.4% sodium hydride is washed three times with petroleum ether and then added to 10 ml. of dimethylformamide while maintaining stirring. To the resulting suspension is added slowly with stirring 1.43 g. of imidazole dissolved in 10 ml. of dimethylformamide resulting in bubbling and an exotherm. After heating the resulting mixture at 40° C. with stirring for 30 minutes the bubbling ceases and then 4.0 g of 2-t-butyl-2-(4-methylphenyl)-oxirane is added followed by heating at 70° C. for 1.5 hours. The resulting reaction mixture is then poured onto water, extracted with ethyl acetate, the organic phase washed with water, dried and evaporated to an oil which is cooled to room temperature to obtain a solid which is recrystallized from hexane/carbon tetrachloride (10:90) to obtain α-t-butyl-α-(p-methylphenyl)-1H-imidazole-1-ethanol, m.p. 135°-137° C.

EXAMPLE 2

Following the procedure of Example 1 the following additional compounds of the invention are obtained:

(A) α-n-butyl-α-(p-methylphenyl)-1H-imidazole-1-ethanol, m.p. 136°-138° C.

(B) α-t-butyl-α-(p-chlorophenyl)-1H-imidazole-1-ethanol.

(C) α-t-butyl-α-(o,p-dichlorophenyl)-1H-imidazole-1-ethanol.

(D) α-t-butyl-α-phenyl-1H-imidazole-1-ethanol.

(E) α-n-propyl-α-(p-methylphenyl)-1H-imidazole-1-ethanol, m.p. 156°-157° C.

(F) α-t-butyl-α-(p-fluorophenyl)-1H-imidazole-1-ethanol.

(G) α-t-butyl-α-(p-methoxyphenyl)-1H-imidazole-1-ethanol.

(H) α-t-butyl-α-(m-nitrophenyl)-1H-imidazole-1-ethanol.

(I) α-t-butyl-α-(m-trifluoromethylphenyl)-1H-imidazole-1-ethanol.

(J) α-t-butyl-α-(m-cyanophenyl)-1H-imidazole-1-ethanol.

(K) α-t-butyl-α-(m,p-methylenedioxyphenyl)-1H-imidazole-1-ethanol.

(L) α-t-butyl-α-(p-biphenylyl)-1H-imidazole-1-ethanol.

(M) α-t-butyl-α-(p-phenoxyphenyl)-1H-imidazole-1-ethanol.

(N) α-i-propyl-α-(p-chlorophenyl)-1H-imidazole-1-ethanol.

(O) α-t-butyl-α-(m,p-dichlorophenyl)-1H-imidazole-1-ethanol.

(P) α-i-butyl-α-(p-methylphenyl)-1H-imidazole-1-ethanol.

(Q) α-n-propyl-α-phenyl-1H-imidazole-1-ethanol, m.p. 119°-120° C.

(R) α-ethyl-α-(p-chlorophenyl)-1H-imidazole-1-ethanol, m.p. 167°-168° C.

(S) α-neopentyl-α-phenyl-1H-imidazole-1-ethanol, m.p. 169°-170° C.

(T) α-cyclopropyl-α-(p-chlorophenyl)-1H-imidazole-1-ethanol, m.p. 132°-134° C.

(U) α-n-pentyl-α-phenyl-1H-imidazole-1-ethanol, m.p. 146°-147° C.

(V) α-cyclopropyl-α-(p-methylphenyl)-1H-imidazole-1-ethanol.

(W) α-cyclopentyl-α-(p-methylphenyl)-1H-imidazole-1-ethanol.

(X) α-t-butyl-α-(p-methylthiophenyl)-1H-imidazole-1-ethanol.

(Y) α-sec.-butyl-α-(p-methylphenyl)-1H-imidazole-1-ethanol.

(Z) α-i-butyl-α-(p-methylphenyl)-1H-imidazole-1-ethanol.

(Z-1) α-t-butyl-α-(m-bromo-p-methylphenyl)-1H-imidazole-1-ethanol.

(Z-2) α-t-butyl-α-(m-fluoro-p-methylphenyl)-1H-imidazole-1-ethanol.

(Z-3) α-t-butyl-α-(m-chloro-p-methylphenyl)-1H-imidazole-1-ethanol.

(Z-4) α-t-butyl-α-(m-chloro-m-methoxyphenyl)-1H-imidazole-1-ethanol.

EXAMPLE 3

Preparation of 2-(t-butyl)-2-(4-methylphenyl)-oxirane

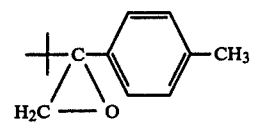

A 2.2 g portion of 61.4% sodium hydride is washed three times with petroleum ether, then 70 ml. of dimethyl sulfoxide added and the mixture heated with stirring to 70° C. and carried to 85° C. by the exotherm after which the mixture is heated at 75° C. for 40 minutes. The resulting mixture is cooled to 0° C. in an ice/salt bath and then under a nitrogen blanket there is added dropwise a solution of 7.0 g. of trimethylsulfonium iodide in 50 ml. of dimethylsulfoxide and 20 ml. tetrahydrofuran while maintaining the temperature below 18° C. To the resulting mixture is then added with stirring under the nitrogen blanket a solution of 3.0 g. of t-butyl p-methylphenyl ketone in 30 ml. of tetrahydrofuran while maintaining the temperature below 10° C. The resulting mixture is stirred at 0° C. for 30 minutes and then at room temperature for 2 hours. The resulting reaction mixture is then poured onto 400 ml. of water, extracted with methylene chloride, the organic phase washed with water and then brine, dried and evaporated to obtain a yellow oil of 2-(t-butyl)-2-(4-methylphenyl)-oxirane.

What is claimed is:
1. A compound of the formula:

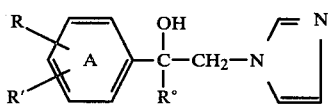

wherein
R° is cycloalkyl of 3 to 6 carbon atoms or cycloalkylalkyl in which the cycloalkyl is of 3 to 6 carbon atoms and the alkyl portion of 1 to 3 carbon atoms, said cycloalkyl and cycloalkylalkyl being optionally ring substituted by one or two alkyl groups of 1 to 3 carbon atoms, and R is hydrogen, fluoro, chloro, bromo, alkyl of 1 to 4 carbon atoms, alkoxy of 1 to 4 carbon atoms, alkylthio of 1 to 4 carbon atoms or nitro, and R' is hydrogen, fluoro, chloro, bromo, alkyl of 1 to 4 carbon atoms, alkoxy of 1 to 4 carbon atoms, alkylthio of 1 to 4 carbon atoms, —$CF_3$ in the 3-position of Ring A, nitro, —CN, —COOR", an optionally substituted phenyl group of the formula:

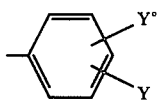

or an optionally substituted phenoxy group in the 4-position of Ring A and having the formula:

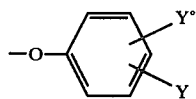

R" is hydrogen, alkyl of 1 to 4 carbon atoms or cation, or

R and R' together represent alkylenedioxy of 1 or 2 carbon atoms substituted onto adjacent carbon atoms of the phenyl Ring A, and Y° and Y are independently hydrogen, fluoro, chloro, bromo, alkyl of 1 to 4 carbon atoms or alkoxy of 1 to 4 carbon atoms.

2. A compound of claim 1 in which R is hydrogen, fluoro, chloro, bromo or $C_1$–$C_4$ alkyl and R' is (a) hydrogen, fluoro, chloro, bromo, $C_1$–$C_4$ alkyl, or $C_1$–$C_4$ alkoxy, or (b) a group located at the para-position of Ring A and having the formula:

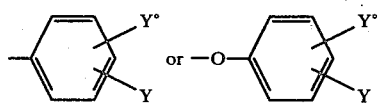

in which Y° and Y are as defined in claim 1.

3. A compound of claim 2 in which R is hydrogen, fluoro, chloro or $C_1$–$C_2$ alkyl and R' is hydrogen, fluoro, chloro, bromo, $C_1$–$C_2$ alkyl or $C_1$–$C_2$ alkoxy.

4. A compound of claim 1, 2, or 3, in which R° is cycloalkyl of 3 to 6 carbon atoms.

5. The compound of claim 1 which is α-cyclopropyl-α-(p-methylphenyl)-1H-imidazole-1-ethanol.

6. The compound of claim 1 which is α-cyclopentyl-α-(p-methylphenyl)-1H-imidazole-1-ethanol.

7. The method of combatting phytopathogenic fungus in plants, seeds or soil comprising treating said plants, seeds or soil with a non-phytotoxic fungicidally effective amount of a compound of claim 1 in which R" when R' is —COOR" is hydrogen, $C_1$–$C_4$ alkyl or an agriculturally acceptable cation and in which the compound when in acid addition salt form is in an agriculturally acceptable acid addition salt form.

8. The method of claim 7 in which R is hydrogen, fluoro, chloro, bromo or $C_1$–$C_4$ alkyl and R' is (a) hydrogen, fluoro, chloro, bromo, $C_1$–$C_4$ alkyl, or $C_1$–$C_4$ alkoxy, or (b) a group located at the para-position of Ring A and having the formula:

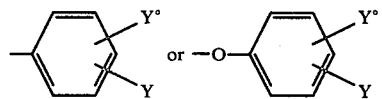

in which Y° and Y are as defined in claim 1.

9. The method of claim 7 in which R is hydrogen, fluoro, chloro or $C_1$–$C_2$ alkyl and R' is hydrogen, fluoro, chloro, bromo, $C_1$–$C_2$ alkyl or $C_1$–$C_2$ alkoxy.

10. The method of claim 7, 8, or 9, in which R° is cycloalkyl of 3 to 6 carbon atoms.

11. The method of claim 7 in which the compound is α-cyclopropyl-α-(p-methylphenyl)-1H-imidazole-1-ethanol.

12. The method of claim 7 in which the compound is α-cyclopentyl-α-(p-methylphenyl)-1H-imidazole-1-ethanol.

13. A fungicidal composition comprising an inert fungicide carrier and a fungicidally effective amount of a compound of claim 1 in which R" when R' is —COOR" is hydrogen, $C_1$–$C_4$ alkyl or an agriculturally acceptable cation and in which the compound when in acid addition salt form is in an agriculturally acceptable acid addition salt form.

* * * * *